United States Patent [19]

Abubaker et al.

[11] Patent Number: 5,888,363
[45] Date of Patent: Mar. 30, 1999

[54] APPARATUS AND METHOD FOR INTERFACING AN OPEN CAPILLARY AND DETECTOR FOR CONDUCTING OFF-COLUMN ANALYSES

[75] Inventors: Mohammad Amin Abubaker, Galveston; Eugene M. Fujinari, Spring; John R. Petersen, Seabrook; Michael G. Bissell, Galveston, all of Tex.

[73] Assignee: Antek Instruments, Inc., Houston, Tex.

[21] Appl. No.: 707,696

[22] Filed: Sep. 3, 1996

[51] Int. Cl.$^6$ .................... G01N 27/26; G01N 27/447
[52] U.S. Cl. .............................. 204/452; 204/603
[58] Field of Search .................... 204/601, 602, 204/603, 604, 605, 451, 452, 453, 454, 455

[56] References Cited

U.S. PATENT DOCUMENTS

| | | | |
|---|---|---|---|
| 3,996,003 | 12/1976 | Fine et al. | 436/107 |
| 4,018,562 | 4/1977 | Parks et al. | 436/114 |
| 5,431,793 | 7/1995 | Wang et al. | 204/452 |

OTHER PUBLICATIONS

Staller, T.D., et al., "Fabrication and Evaluation of PostCapillary Junctions via Micro–Scale Molding for Use as Reactors and Flow Multiplexers in Capillary Electrokinetic Separations," Instrumentation Science & Technology, 23(4) :235–254 (1995).

Latva, M., et al., "Time–resolved Luminescence Detection of Europium (III) Chelates in Capillary Electrophoresis." Analyst, 120:367–372 (Feb. 1995).

Daddo, R., et al., "End–Column Chemiluminescence Detector for Capillary Electrophoresis," Analytical Chemistry, 66(2) :303–306 (Jan. 1994).

Smith, R.D., et al., "Capillary Electrophoresis/Mass Spectrometry", Analytical Chemistry, 65(13) :574–584 (Jul. 1993).

Ruberto, M.A., et al., "Acridinium Chemiluminescence Detection with Capillary Electrophoresis," Analytical Chemistry, 64(22) :2758–2762 (Nov. 1992).

(List continued on next page.)

Primary Examiner—William H. Beisner
Assistant Examiner—John S. Starsiak, Jr.
Attorney, Agent, or Firm—Vaden, Eickenroht & Thompson, L.L.P.

[57] ABSTRACT

An apparatus and method for interfacing a capillary with a detector is disclosed. In particular, a capillary that is used in a capillary electrophoresis technique is interfaced with an off-column detector that is destructive of the sample or that will otherwise create adverse affects on the operations of the capillary electrophoresis. By way of example only, a nitrogen chemiluminescent detector using pyro-chemiluminescent techniques is discussed. An interface between the separation and detection systems is essential to prevent interference between the two systems. The interface apparatus and method are achieved by creating a closed connection between the two systems within which the pressure and sample flow rate can be controlled. Pressure control is achieved through the introduction and venting of gas into and from the integrated system. Interference between interfaced systems is then prevented by equalizing the pressure in the interface apparatus with the head pressure on the inlet end of the capillary. Also disclosed is a device for controlling the head pressure and sample flow within the capillary thereby enabling operation of an interfaced system at non-atmospheric pressure conditions.

27 Claims, 4 Drawing Sheets

OTHER PUBLICATIONS

Courthaudon, L.O., et al., "Nitrogen–specific Gas Chromatography Detection Based on Chemiluminescence," LC.GC, vol. 9, No. 10 (No date available).

Fujimari, E.M., et al., "Nitrogen–Specific Gas Chromatography Detection Based on Chemiluminescence –Application to the Analysis of Ammonium Nitrogen in Waste Water," Journal of Chromotography, 592:209–214 (1992).

Albin, M., et al., "Fluorescence Detection in Capillary Electrophoresis: Evaluation of Derivatizing Reagents and Techniques," Analytical Chemistry 63:417–422 (Mar. 1991).

Huang, X., et al., "End–Column Detection for Capillary Zone Electrophoresis," Analytical Chemistry 63(2):189–192 (Jan. 1991).

Britten, A.J., "Can Your G. C. System Find Nitrogen inthis Flower? Chemiluminescent detection makes it possible to isolate nitrogen in co–eluting compound such as pesticides." Research & Development, Sep. 1989, pp. 77–80.

Huang, X., et al., "On–Column Conductivity Detector for Capillary Zone Electrophoresis", Analytical Chemistry, 59(23):2747–2749 (Dec. 1987).

Walbroehl, Y., et al., "On–Column UV Absorption Detector for Open Tubular Capillary Zone Electrophoresis", Journal of Chromatography, 315:135–143 (1984).

Jorgenson, J.W., et al., "Zone Electrophoresis in Open–tubular Glass Capillaries", Analytical Chemistry, 53(8):1298–1302 (Jul. 1981).

Qinghong Lu et al., "Interface for Capillary Electrophoresis and Inductively Coupled Plasma Mass Spectrometry" Analytical chemistry vol. 67, No. 17 (01 Sep. 1995) 2949–2956.

Wim Th. Kok et al., "Post–column reaction system for fluorescence detection in capillary electrophoresis" Journal of Chromatography A, 716 (17 Nov. 1995) 123–133.

Wim Th. Kok, "Off–column Detection with Pressure Compensation in Capillary Electrophoresis" Analytical Chemistry, vol. 65, No. 14, (15 Jul. 1993) 1853–1860.

Wim Th. Kok, "Determination of sugars by capillary electrophoresis with electrochemical detection using cuprous oxide modified electrodes" Journal of Chromatography A, 707, No. 2 (21 Jul. 1995) 335–342.

PEAKS:
A = L-PHENYLALANINE
B = PARA-AMINO
    SALICYLIC ACID

PEAKS:
A = L-PHENYLALANINE

PEAK:
B = PARA-AMINO
    SALICYLIC ACID

APPARATUS AND METHOD FOR INTERFACING AN OPEN CAPILLARY AND DETECTOR FOR CONDUCTING OFF-COLUMN ANALYSES

BACKGROUND OF THE INVENTION

1. Field of the Invention

The field of this invention is instrumental chemistry as it relates to integrated systems for carrying out combined separation and analytical operations. More specifically, this invention relates to an apparatus and method for integrating a capillary electrophoresis apparatus with an off-column detection system, particularly detection systems using pyrochemiluminescent techniques.

2. Description of the Prior Art

Capillary electrophoresis (CE) has been highly praised for its capacity to separate sample components using only minute volumes of sample and reagents and yet providing highly resolved separations in extremely short analysis times. The limitation of this technique lies in the relatively few means available with which to conduct highly sensitive analyses on those separated sample components. At present, on-line detection techniques employed with CE can be described based on the location of their analysis as on-column, end-column or off-column.

On-column analytical methods are typically conducted across the capillary either through a window or an opening provided in the capillary wall. On-column techniques such as ultraviolet-visible absorption are in common use because they do not interfere with the separatory operation of the CE and require simple instrumentation. However, as is described in *Analyst*, "Time-resolved Luminescence Detection of Europium(III) Chelates in Capillary Electrophoresis," Latva, M. et al., Vol. 120, 367–372 (February 1995), the detection limits of the absorption methods are poor due to their dependence on optical path length which is very short across the capillary. The inner diameter of the capillary of a CE is typically in the range of 25 to 100 micrometers.

Alternatively, on-column amperometric detection may provide relatively good detection limits. However, periodic cleaning of the working electrode is required to maintain the detector's performance. This cleaning requirement is accompanied by the additional problem of electronically isolating the working electrode from the high potential field that is applied across the CE capillary during its operation. One solution for isolating the working electrode from the applied potential is to convert the on-column amperometric technique to an end column method. As is described in *Analytical Chemistry*, "End-Column Detection for Capillary Zone Electrophoresis," Huang, X. and Zare, R. N., Vol. 63, 189–192 (1991) the working electrode may be completely removed from the potential field of the CE by locating a microelectrode adjacent the capillary outlet at the end of the column. However, Huang recognizes that although this arrangement resolves the isolation problem, it is accompanied by losses in both sensitivity and resolution.

Fluorescence is another photometric method for conducting on-column analyses. Conventional fluorescent methods are described in *Analytical Chemistry*, "Fluorescence Detection in Capillary Electrophoresis: Evaluation of Derivatization Reagents and Techniques," Albin, M. et al., Vol. 63, 417–422 (1991). It is well established that although fluorescent methods can be highly sensitive and selective, the techniques require that the sample components be fluorescent or chemically convertible to a fluorescing compound. These tagging and/or derivatization procedures can be particularly difficult when performed at the low analyte concentrations that are characteristic of CE. Further, these processes can be complex and greatly increase the risk of contaminating the sample. It is also noteworthy with respect to laser induced fluorescence, that the number of fluorescing compounds available for derivatization procedures is further limited by the number of excitation wavelengths of available lasers.

The problem that accompanies any attempt to integrate two or more systems is the interfering effect the systems may have on one another. Background on the mechanism by which CE separates samples into individual components is helpful in understanding the problems that accompany the integration of CE with an off-column detection system.

CE separates the components of a sample on the basis of the electrical properties of those components. A capillary, typically of fused silica, is filled with an ionic buffer solution and the ends of the capillary are emersed in reservoirs containing additional buffer solution. Electrodes are provided at the opposite ends of the capillary and a high voltage potential in the range of 20 to 30 kilovolts is applied. The sample components are caused to migrate under the influence of the applied potential in what is commonly referred to as electroosmotic flow. The unique feature of electroosmotic flow is that it produces a flat profile in the migrating sample across the capillary. Conversely, when a sample is driven through a capillary by hydrostatic pressure, the sample front will have a parabolic profile which increases the occurrence of band broadening and diminishes resolution. The flat profile generated by CE provides enhanced resolution in sample separation over and above that obtainable from chromatographic techniques. Naturally, any convection, currents or pressure differentials existing or created within the CE system will adversely affect the flat profile of the sample as it travels through the capillary. In order to avoid these adverse affects most detection systems employed with CE use either an on-column or end-column approach.

Detectors and methods that require the analyte to be transferred from the capillary outlet to a detector for analysis are referred to as off-column systems. Off-column systems are less known in the art because the connections between the capillary outlet and the detection systems have introduced problems that interfere with the separatory operation of the CE. In addition to the problems discussed above, transfer of CE eluent for off-column detection may include the problems of dead volume and band dispersion due to turbulence and/or resistances to mass transfer. Further still, the transfer is complicated by the fact that the volume of CE eluent will typically be only in the nanoliter range.

*Instrumentation Science & Technology*, "Fabrication And Evaluation Of Post-Capillary Junctions Via Micro-scale Molding For Use As Reactors And Flow Multiplexers In Capillary Electrokinetic Separations," Staller, T. D. and Sepaniak, M. J., 23(4), 235–254 (1995) describes methods for making and using junctions for integrated systems. The junctions are molded from polymers such as polyimides and epoxys. Specifically, the CE in Staller is integrated with a chemiluminescent/fluorescent technique wherein the chemiluminescent reaction occurs within the molded junction and the light generated by the reaction is transferred by optical fiber to a photomultiplier tube for detection. The problems of dead volume and turbulence due to the addition of reagents are addressed in terms of the geometries of the junction's structure. The junction between the CE and the detection apparatus is described as a closed system, and no means are suggested or disclosed for preventing pressure differentials across the junction or between the CE and detector instrumentation.

Earlier efforts directed at coupling CE to a detector for conducting off-column analysis have been with respect to mass spectrometry, or CE-MS systems. These developments are well documented in *Analytical Chemistry*, "Capillary Electrophoresis/Mass Spectrometry," Smith, R. D. et al., Vol. 65, No. 13 (Jul. 1, 1993). The CE-MS systems developed have largely relied on an electrospray ionization (ESI) method in which the CE eluent is converted to an electrospray that can be drawn into the mass spectrometer by a high vacuum provided at the mass spectrometer inlet. Recent developments have focused on eliminating the sheathing solution that is used to facilitate the conversion of the CE eluent to a spray. However, because the mass spectrometer operates under an extremely high vacuum, these integrated systems are not capable of controlling the pressure within the interfacing apparatus. Further, these systems generally require a gap between the nebulizer and inlet to the mass spectrometer and thus do not provide a closed interface between the two instruments.

Therefore it is a feature of the present invention to provide an apparatus and method for interfacing a capillary electrophoresis apparatus with an off-column detection system that will not create convection, currents or pressure differentials that would otherwise adversely affect the electroosmotic flow in the capillary of the CE.

It is another feature of the present invention to provide an apparatus and method for interfacing a CE apparatus with an off-column detection system of the type described above in which the pressure within the interfacing apparatus may be adjusted by the introduction and venting of gases of which one may be an inert gas.

It is yet another feature of the present invention to provide an apparatus and method for interfacing a CE apparatus with an off-column detection system of the type described above in which an exit housing is attached to the capillary above the capillary outlet wherein a flow of ionic sheathing buffer is used to complete the electrical circuit of the CE apparatus and to carry the CE eluent into the off-column detector apparatus.

It is still yet another feature of the present invention to provide an apparatus and method for interfacing a CE apparatus with an off-column detection system of the type described above in which the detector is a chemiluminescent detector utilizing pyro-chemiluminescent technique, the furnace of which introduces pressure variations within the interface apparatus which would otherwise interfere with the operation of the CE.

It is still yet another feature of the present invention to provide an apparatus and method for interfacing a capillary electrophoresis apparatus with an off-column detection system of the type described above in which the head pressure at the inlet of the capillary of the CE is equalized with the pressure within the interface apparatus so that a pressure gradient or differential is not created within the CE capillary.

It is still another feature of the present invention to provide an apparatus and method for interfacing a capillary electrophoresis apparatus with an off-column detection system of the type described above in which the head pressure at the capillary inlet of the CE apparatus is controlled so that analyses may be performed at other than atmospheric pressure conditions.

BRIEF DESCRIPTION OF THE DRAWINGS

So that the manner in which the above-recited features, advantages and objects of the invention, as well as others which will become clear, are attained and can be understood in detail, more particular description of the invention briefly summarized above may be had by reference to the exemplary preferred embodiments thereof which are illustrated in the appended drawings, which form a part of this specification. It is to be noted, however, that the drawings illustrate only typical preferred embodiments of the invention and are therefore not to be considered limiting of its scope as the invention may admit to other equally effective embodiments.

DETAILED DESCRIPTION OF THE INVENTION

The development of the present invention is directed to interfacing a capillary electrophoresis (CE) apparatus with a chemiluminescent nitrogen detector (CLND) that is capable of detecting chemically bound nitrogen in organic compounds. It is anticipated that this integrated CE-CLND system will have significant commercial value in that it is appropriate for use in clinical, pharmaceutical, industrial, educational and environmental fields. However, the scope of the present invention is not limited to a CE integrated with an off-column nitrogen detector but will include other off-column detectors including without limitation those capable of analyzing carbon compounds using infrared methods, chlorine and fluorine compounds using element selective electrodes and sulfur compounds using sulfur chemiluminescent methods.

Figure 1:
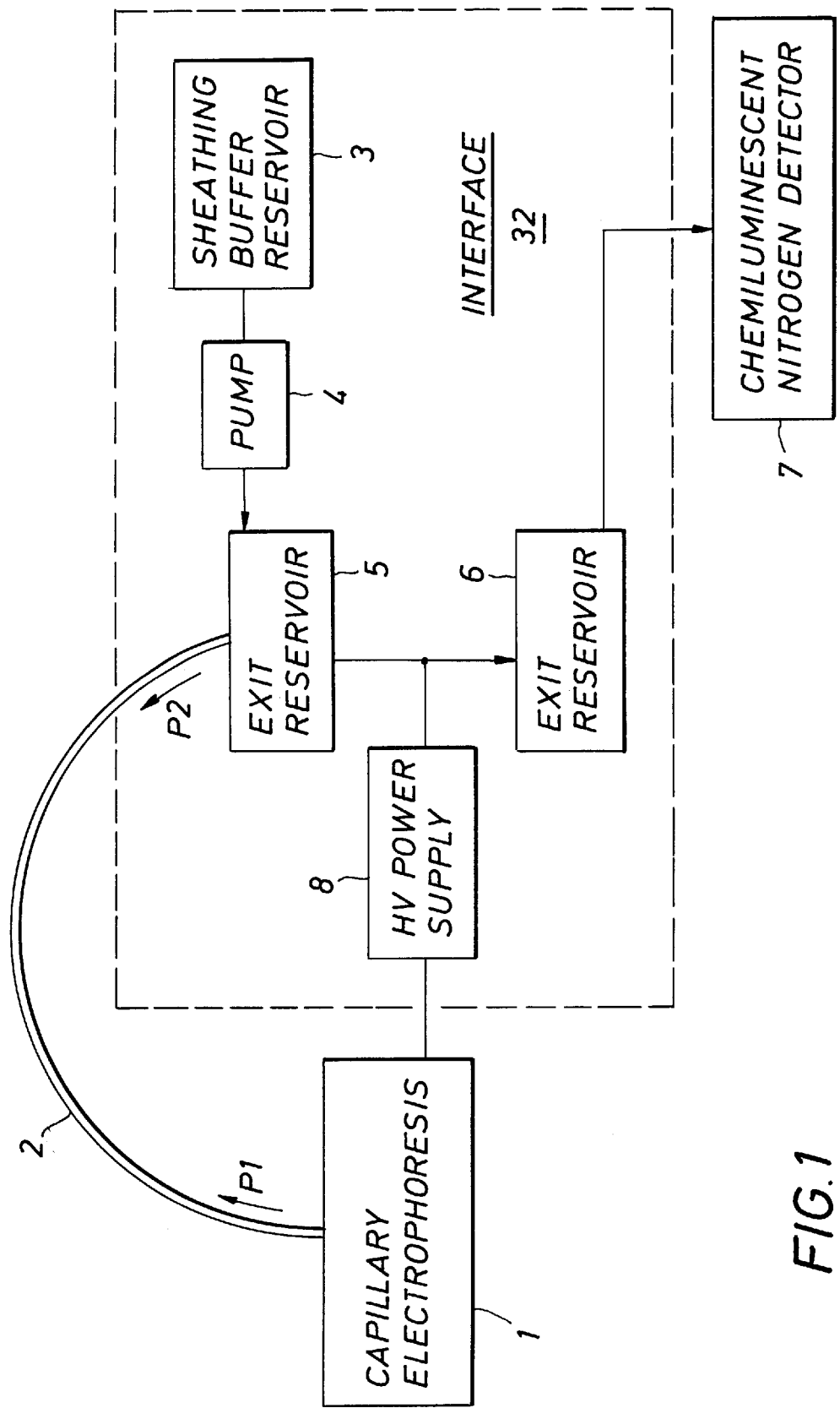
FIG. 1 is a schematic view of an integrated capillary electrophoresis—chemiluminescent nitrogen detector in accordance with the present invention.

Now referring to the drawings, FIG. 1 is a schematic representation of an apparatus of the present invention. A capillary electrophoresis apparatus, noted generally at reference number 1, has capillary 2 that is made from open blank fused silica capillary tubing approximately 80 centimeters in length and having an inner diameter of 50 micrometers. The inner surface of capillary 2 may optionally be coated with a suitable stationary phase as determined by the sample to be separated. For instance, when using the apparatus of the present invention to separate and analyze proteins it is preferable that the inner surface of capillary 2 be coated with a stationary phase containing amino groups (—$NH_2$).

Figure 2:
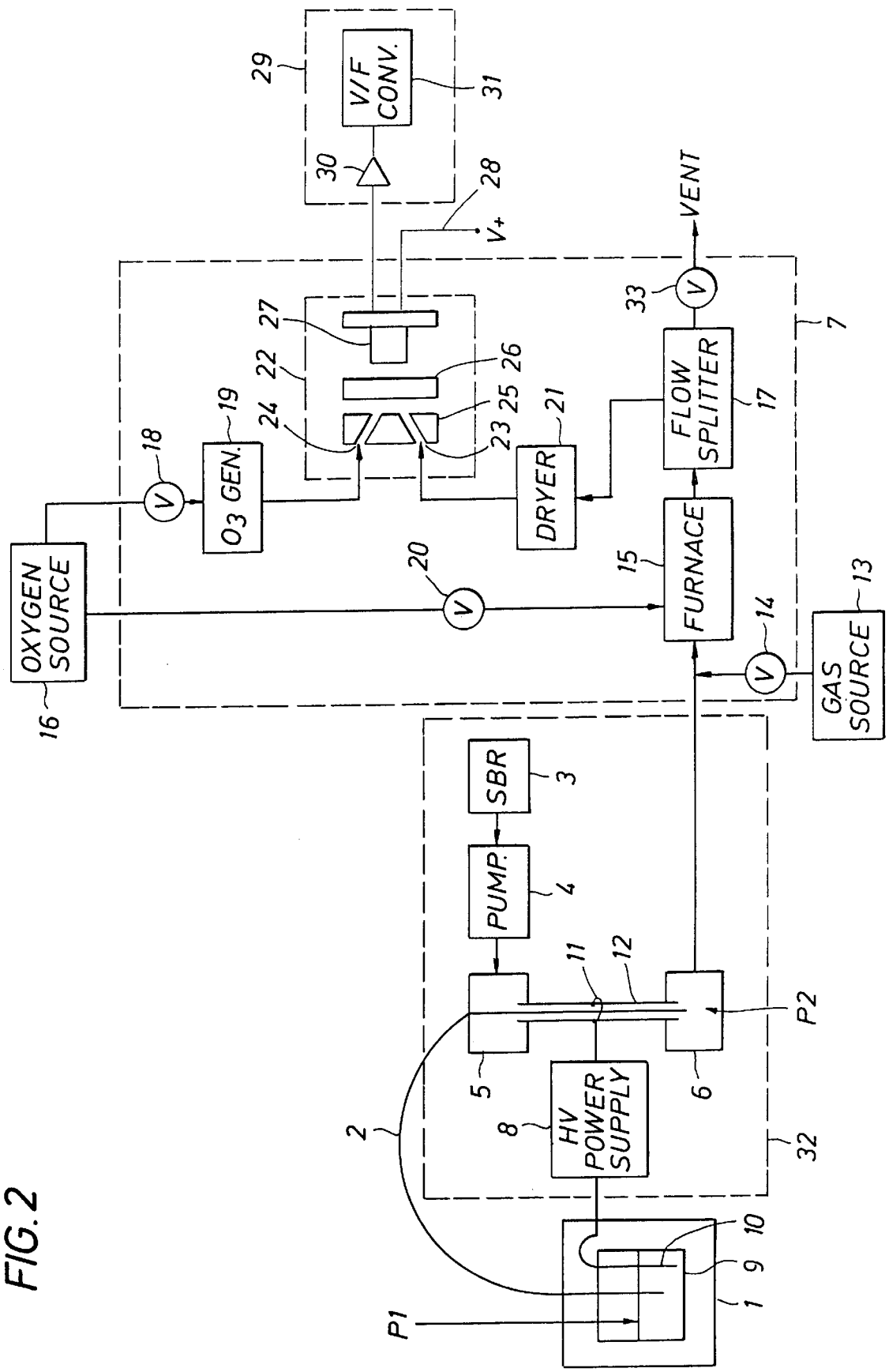
FIG. 2 is a detailed diagrammatic view of an integrated capillary electrophoresis—chemiluminescent nitrogen detector in accordance with the present invention.

As shown in more detail in FIG. 2, the CE apparatus includes the inlet of capillary 2 emersed in a reservoir containing ionic buffer solution 9. Reference number P1 indicates the head pressure on ionic buffer solution 9 and thus the pressure at the capillary inlet. Also in contact with ionic buffer solution 9 is electrode 10. In a typical CE analysis, electrode 10 would be the positive electrode while the electrode at the outlet, electrode 12, would be the negative electrode. In this arrangement, the sample components will be separated according to their electronic properties and the components bearing positive charges will emerge from the capillary first, followed by the neutral components and then the negatively charged components.

Electrodes 10 and 12 are arranged at opposite ends of capillary 2 and a potential of about 30 kilovolts is applied by high voltage power source 8. This voltage level will result in a steady current of nearly 10 microamps. The circuit between the electrodes is completed through capillary 2 by ionic buffer solution 9 that fills the capillary. This solution may be any ionic buffer. An example of this invention using a solution consisting of 0.3% sodium borate and 0.4% boric acid in water is presented herein. The results of this example are presented graphically as FIGS. 4a, 4b and 4c.

Detector 7 in FIG. 1 is a chemiluminescent nitrogen detector that is connected to the CE via the interfacing apparatus. As noted above, the specific type of detection system employed will depend upon the chemical element or compound that is of interest. While it is anticipated that almost any type of detector may be interfaced with CE using an apparatus of the present invention, those off-column detectors that are destructive of the sample such as those which employ furnaces as in pyro-chemiluminescent techniques and those which require that the sample be volatilized in carrying out the analysis will receive the greatest benefit from the apparatus and method of the present invention. The adverse effects of these types of detectors on the CE operation can be minimized if not eliminated altogether.

Interfacing apparatus 32 is shown in more detail in FIG. 2 and is composed of a number of elements that complete and maintain the electrical circuit of the CE and provide a carrier for the CE eluent. Sheathing buffer reservoir 3 contains a sheathing buffer which is preferably identical to ionic buffer solution 9. Pump 4 is utilized to deliver an adjustable flow of sheathing buffer to exit housing 5. Pump 4 should have flow rates adjustable from 1 to at least 500 microliters per minute. Exit housing 5 is shown as a cylindrical structure that encloses the lower end of capillary 2 and forms a closed connection between the capillary 2 and detector 7. However, the configuration of exit housing 5 should not be considered to be restricted to this cylindrical structure. Housing 5 is attached to the external surface of the capillary 2 above capillary outlet 6 and extends below that outlet to connect with detector inlet 35.

Electrode 12 of the CE is attached to high voltage power supply 8 via electrical lead 11. Electrode 12 is attached to the external surface of capillary 2 just above capillary outlet 6. The electrical connection and thus the potential applied across capillary 2 is maintained by the flow of sheathing buffer that is directed across electrode 12 and across capillary outlet 6. Reference P2 is the pressure within interface apparatus 32 adjacent capillary outlet 6.

As shown in FIG. 2, capillary outlet 6 is in fluid communication with the furnace 15 of detector 7 via detector inlet 35. CE eluent is carried away from the capillary outlet 6 as it emerges from the outlet. The eluent is carried out of the exit housing and into detector inlet 35 leading directly into furnace 15. Also connected to inlet 35 is inert gas source 13. The flow of gas from source 13 is controlled by valve 14. Further, furnace 15 is connected to oxygen source 16 with the flow of oxygen controlled by valve 20.

Connected to furnace 15 is flow splitter 17. Splitter 17 is capable of directing the combusted products exiting the furnace to dryer 21 and through valve 33 to an exit vent. The dried combusted products are then directed to detector assembly 22 where they pass through porthole 23 located in the wall of reaction chamber 25. Entering chamber 25 through porthole 24 is ozone ($O_3$) that has been generated by ozone generator 19. Ozone generator 19 is supplied with oxygen ($O_2$) by oxygen supply source 16, the flow from source 16 being regulated by valve 18.

Where the CE has been used to separate nitrogen containing compounds, the combustion products of furnace 15 will include nitric oxide gas that will react with the ozone in reaction chamber 25. The products of this reaction are nitrogen dioxides in the excited state. As the excited nitrogen dioxides relax to the ground state, they spontaneously emit photons in an amount that is proportional to the number of nitrogen atoms in the components of the CE separation. The radiation of the photons passes through filter 26 which allows the passage of light having wavelengths within the range of 600 to 900 nanometers. The light that passes through filter 26 is detected by photomultiplier tube 27 which generates an electrical signal which is sent to signal integrator 29. Integrator 29 includes amplifier 30 and V/F converter 31.

Figure 3:
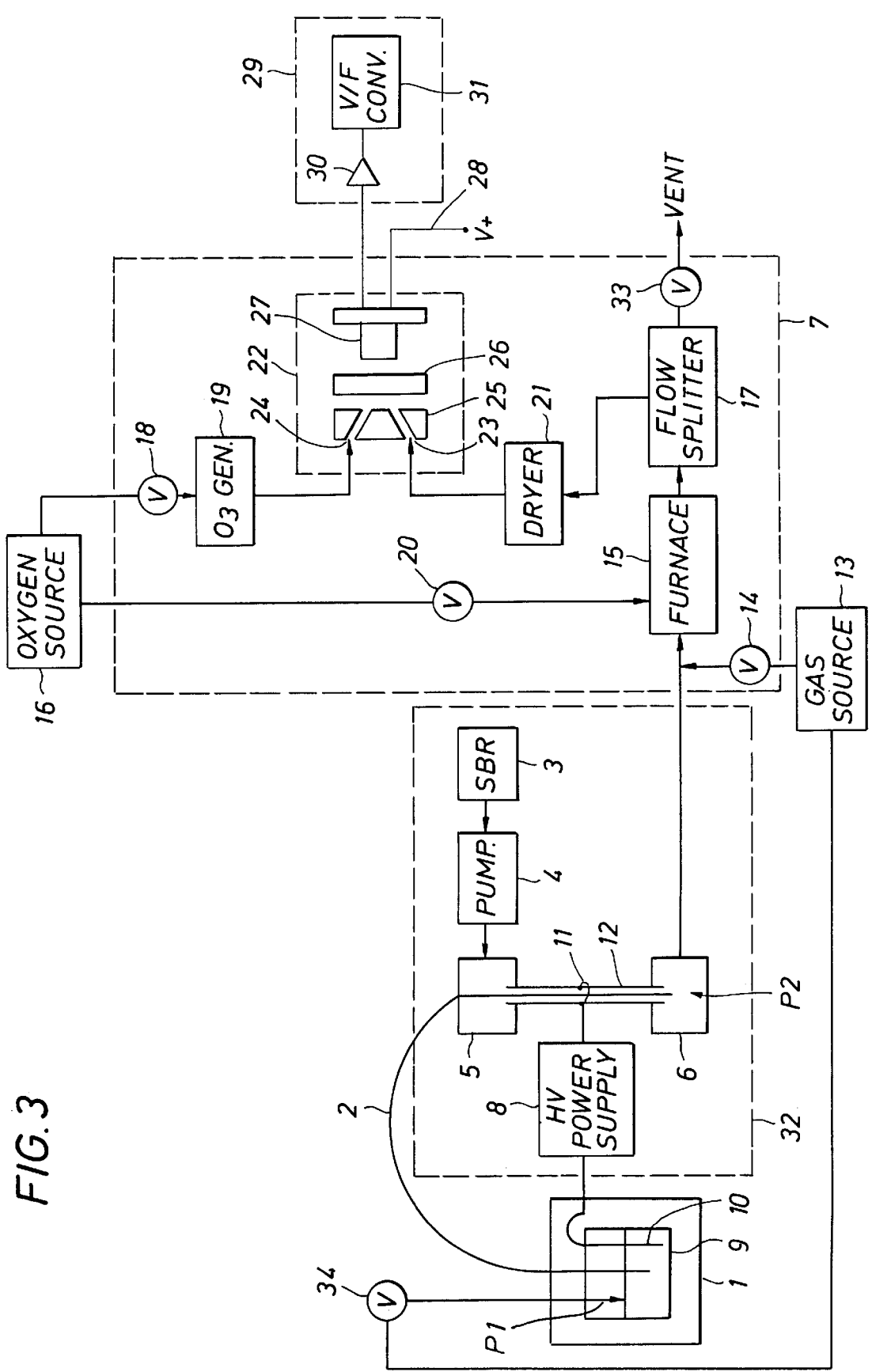
FIG. 3 is a detailed diagrammatic view of an integrated capillary electrophoresis—chemiluminescent nitrogen detector in accordance with the present invention wherein means are provided for controlling the head pressure at the capillary inlet.

Variations in pressure within interface 32 are mostly due the operation of furnace 15. The pressure inside the furnace may under one operating condition result in a back-flush of positive pressure causing P2 to be greater than P1, and under another operating condition, generate negative pressure that causes P1 to be greater than P2. In either case, the electroosmotic flow is adversely affected and little or no separation of sample components can be obtained from the CE. There are several means disclosed in the present invention with which to adjust the pressure within a closed interface between CE and detector apparatuses. Variables affecting the pressure within interface 32 include the flow rate of the sheathing buffer as controlled by pump 4, the flow rate of inert gas from source 13 into inlet 35, the oxygen flow rate from source 16 and the rate at which combusted products are removed from furnace 15. With respect to the removal of combusted products from the furnace, as shown in FIGS. 2 and 3, flow splitter 17 and valve 33 are provided for diverting a portion of the combusted products from the furnace directly to an exit vent. By opening valve 33 and directing a portion of the combusted products to the outside vent, the internal pressure within furnace 15 is reduced and the potential for back flush is removed. Additional adjustments of the other variables affecting the interface pressure may be required to balance P2 with P1. When this balance is achieved, the separatory operation of the CE will not be interrupted by the operation of the furnace or some other off-column detector.

As shown in FIG. 3, pressure control means may also be used to adjust the head pressure on the ionic buffer solution 9 at the capillary inlet. Gas source 13 is shown to be connected to the closed reservoir containing buffer solution 9. Gas source 13 is preferably an inert gas, however, it may also be oxygen, air or any mixture thereof. Valve 34 is shown as the means for controlling the flow of inlet gas from source 13 into the reservoir. Not shown is a vent to the reservoir which may be used to release excess head pressure. Conventional CE operations using open capillary tubing is conducted with inlet and outlet reservoirs largely open to atmospheric conditions. By having a closed system and means for controlling and balancing pressures at either end of the CE apparatus, the integrated separation and analysis technique of the present invention may be performed at conditions varying from standard and/or atmospheric without adversely affecting the function of the individual systems.

Figure 4A:
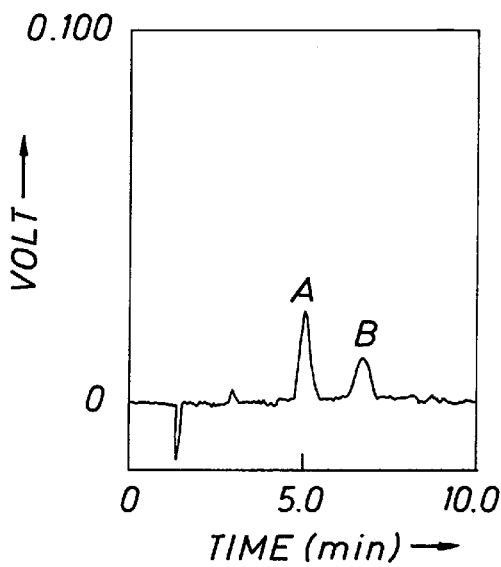
FIG. 4a is a graphical representation of the results of an analysis of a sample solution containing L-phenylalanine and para-amino salicylic acid as conducted on the apparatus of FIG. 2.

FIG. 4a is a graphical representation of results obtained from an apparatus having the features of the present invention. In the procedure employed in obtaining FIG. 4a, an open capillary tube approximately 80 centimeters in length and having an inner diameter of 50 micrometers was used. The CE apparatus was obtained from Helena Laboratories of Beaumont, Tex., and the chemiluminescent nitrogen detector is manufactured by Antek Instruments, Inc. of Houston, Tex. The separation and detection results achieved using the principles of the present invention were confirmed by results obtained from identical analyses performed on sample standards. These confirming results are presented graphically in FIGS. 4b and 4c.

The ionic buffer solution was a 0.3% sodium borate and 0.4% boric acid in water. A discrete sample of a solution containing the amino acid, L-phenylalanine, and para-amino salicylic acid was injected into the capillary inlet. The inlet of capillary 2 was then emersed in ionic buffer solution 9. Pressure at P1 and P2 was adjusted to about 50 millibars. Equalization at this pressure was obtained by adjusting the head pressure on the ionic buffer solution at the capillary inlet, adjusting the flow rate of the sheathing buffer into exit housing 5 and by adjusting the opening at flow spitter 17 for products coming off the furnace. Generally, to reduce the pressure at P2 to a satisfactory level it was found that flow splitter 17 should be substantially open so that a large amount of combustion gases are directed out of the furnace.

A voltage of 30 kilovolts was applied to the capillary to induce the electroosmotic flow. The measured current obtained from the applied potential was a steady 9.8 microamps. The flow rate of the sheathing buffer was adjusted to be sufficiently high to maintain the electrical circuit and to carry the CE eluent into the detector apparatus. However, as noted above the contribution of the flow rate to the pressure within the interface apparatus should be the determining factor regarding the sheathing buffer flow rate.

Figure 4B:
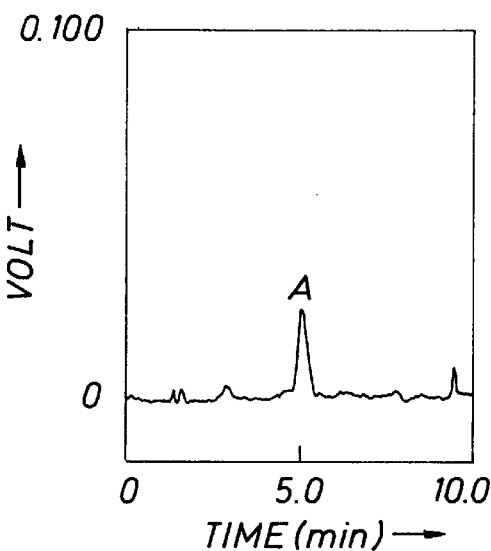
FIG. 4b is a graphical representation of the results of an analysis of a sample containing a standard solution of L-phenylalanine as conducted on the apparatus of FIG. 2.
Figure 4C:
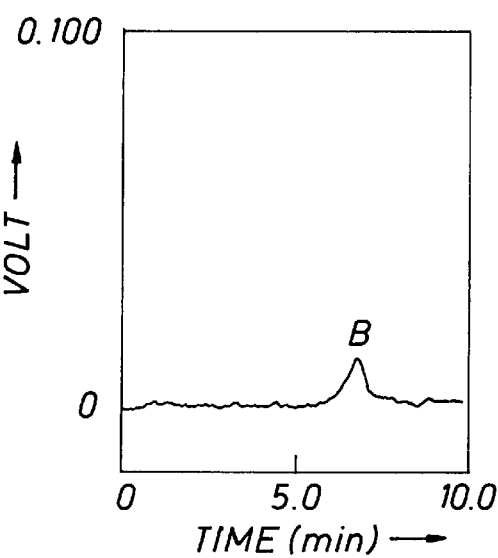
FIG. 4c is a graphical representation of the results of an analysis of a sample containing a standard solution of para-amino salicylic acid as conducted on the apparatus of FIG. 2.

The results of the separation and analysis of the L-phenylalanine/para-amino salicylic acid solution are presented graphically in FIG. 4a. Peak A represents the L-phenylalanine component of the sample solution while peak B represents the para-amino salicylic acid component. The identity of these peaks is confirmed by the separate analyses performed on standards of these two components using the same procedure and conditions. The results of these two additional analyses are presented in FIGS. 4b and 4c, representing L-phenylalanine and para-amino salicylic acid respectively.

In terms of the method of the present invention, off-column detection is shown to be a reliable and accurate method for conducting an integrated analysis following sample separation by CE. This analysis is made possible by creating a closed system that interfaces the instrumentation of the two systems and allows for pressure control either within the interface or more preferably within the interface and at the CE inlet. It is this pressure control that enables pressure equalization at either end of the CE apparatus and compensates for any adverse affects originating from the operations of an integrated detector.

Further additional optional embodiments can be chosen by using pyro-chemiluminescent detector 7 directed to different chemical elements and by using different types of detectors which would otherwise interfere with the operation of the CE 1 without the closed pressure controlled interface 32 in accordance with the present invention. However, the general principles of operation are applicable as discussed above even though the combinations available are more complex. Thus while several embodiments have been discussed and other embodiments have been generally described, it is understood that the invention is not limited thereto, since many modifications may be made and will become clear to those skilled in the art.

What is claimed is:

1. An apparatus for interfacing an open capillary to a detector for conducting off-column analyses, the apparatus comprising:

a housing connected to the capillary tube above the outlet of the capillary;

a source of sheathing buffer connected to the housing;

means for controlling the flow of sheathing buffer into the housing and onto the capillary;

means for controlling the pressure in the housing wherein said pressure control means is a source of gas and/or a flow splitter connected downstream of the capillary outlet; and an outlet to a detector connected to the housing adjacent the capillary outlet.

2. The interface apparatus of claim 1 wherein the means for controlling the flow of sheathing buffer into the housing is a pump.

3. The interface apparatus of claim 1 further comprising means for controlling the pressure at the inlet of the capillary.

4. The interface apparatus of claim 3 wherein the means for controlling the pressure at the capillary inlet is a source of gas connected upstream of the capillary inlet.

5. The interface apparatus of claim 1 wherein the capillary is being used for conducting capillary electrophoresis.

6. An apparatus for interfacing an open capillary with an off-column detector having a furnace, the apparatus comprising:

a housing connected to the capillary above the outlet of the capillary, the housing including an electrode attached to the outside surface of the capillary adjacent the outlet;

a source of sheathing buffer connected to the housing;

means for controlling the flow of sheathing buffer into the housing and onto the electrode;

means for controlling the pressure in the housing; and a housing outlet connected to a detector having a furnace.

7. The interface apparatus of claim 6 wherein the means for controlling the flow of sheathing buffer into the housing is a pump.

8. The interface apparatus of claim 6 wherein the means for controlling the pressure in the housing is a source of gas located downstream of the capillary outlet.

9. The interface apparatus of claim 6 wherein the means for controlling the pressure in the housing is a flow splitter located downstream of the capillary outlet.

10. The interface apparatus of claim 6 further comprising means for increasing the pressure at the capillary inlet.

11. The interface apparatus of claim 10 wherein the means for increasing the pressure at the capillary inlet is a source of gas connected upstream of the capillary inlet.

12. The interface apparatus of claim 6 wherein the capillary is being used for conducting capillary electrophoresis.

13. A method for interfacing an open capillary to a detector for conducting off-column analyses comprising the steps of:

enclosing the outlet end of the capillary in an housing;

providing a stream of sheathing buffer into the housing;

controlling the flow of sheathing buffer into the housing and onto the capillary;

controlling the pressure in the housing by adjusting a flow of a gas introduced downstream of the capillary outlet and/or adjusting an opening on a flow splitter located downstream of the capillary outlet; and connecting a detector to the housing adjacent the capillary outlet.

14. The method of claim 13 wherein the sheathing buffer is an ionic buffer.

15. The method of claim 14 wherein the buffer comprises 0.3% sodium borate and 0.4% boric acid in water.

16. The method of claim 13 wherein the flow of sheathing buffer is in the range of 1 to 500 microliters per minute.

17. The method of claim 13 wherein the open capillary separates sample components using electroosmotic flow.

18. A method for interfacing an open capillary with a detector having a furnace for conducting off-column analyses, comprising the steps of:

enclosing the outlet end of the capillary in an housing;

providing a stream of sheathing buffer into the housing;

controlling the flow of sheathing buffer into the housing and onto the electrode;

controlling the pressure in the housing; and connecting a detector having a furnace to the housing adjacent the capillary outlet.

19. The method of claim 18 wherein the sheathing buffer is an ionic buffer.

20. The method of claim 19 wherein the buffer comprises 0.3% sodium borate and 0.4% boric acid in water.

21. The method of claim 18 wherein the flow of sheathing buffer is in the range of 1 to 500 microliters per minute.

22. The method of claim 18 wherein the pressure in the housing is controlled by adjusting the flow of a gas introduced downstream of the capillary outlet.

23. The method of claim 18 wherein the pressure in the housing is controlled by adjusting the opening on a flow splitter located downstream of the capillary.

24. The method of claim 18 further comprising the step of controlling the pressure at the inlet of the capillary.

25. The method of claim 24 wherein the pressure at the capillary inlet is controlled by adjusting a flow of a gas introduced upstream of the capillary inlet.

26. An apparatus for interfacing an open capillary to a detector for conducting off-column analyses, the apparatus comprising:

a housing connected to the capillary tube above the outlet of the capillary;

a source of sheathing buffer connected to the housing;

means for controlling the flow of sheathing buffer into the housing and onto the capillary;

means for controlling the pressure in the housing;

means for increasing pressure at the inlet of the capillary; and an outlet to a detector connected to the housing adjacent the capillary outlet.

27. A method for interfacing an open capillary to a detector for conducting off-column analyses comprising the steps of:

enclosing the outlet end of the capillary in an housing;

providing a stream of sheathing buffer into the housing;

controlling the flow of sheathing buffer into the housing and onto the capillary;

controlling the pressure in the housing;

controlling the pressure at the capillary inlet by adjusting the flow of gas introduced upstream of the capillary inlet; and connecting a detector to the housing adjacent the capillary outlet.

* * * * *